United States Patent
Fink-Jensen et al.

(10) Patent No.: US 6,211,173 B1
(45) Date of Patent: Apr. 3, 2001

(54) USE OF 2,3,4,5-TETRAHYDRO-1H-3-BENZAZEPINES FOR THE MANUFACTURE OF A PHARMACEUTICAL COMPOSITION FOR THE TREATMENT OF SLEEP DISORDERS

(75) Inventors: Anders Fink-Jensen, Copenhagen; Christian Foged, Birkerød, both of (DK)

(73) Assignee: Cenes Limited, Cambridge (GB)

( * ) Notice: Subject to any disclaimer, the term of this patent is extended or adjusted under 35 U.S.C. 154(b) by 0 days.

(21) Appl. No.: 09/380,840

(22) PCT Filed: Mar. 11, 1998

(86) PCT No.: PCT/DK98/00088

§ 371 Date: Nov. 18, 1999

§ 102(e) Date: Nov. 18, 1999

(87) PCT Pub. No.: WO98/40072

PCT Pub. Date: Sep. 17, 1998

Related U.S. Application Data

(60) Provisional application No. 60/041,509, filed on Mar. 24, 1997.

(30) Foreign Application Priority Data

Mar. 12, 1997 (DK) .................................................. 0265/97

(51) Int. Cl.[7] .................................................. A61K 31/55
(52) U.S. Cl. .................................................. 514/213.1
(58) Field of Search .................................................. 514/213

(56) References Cited

U.S. PATENT DOCUMENTS

| | | | |
|---|---|---|---|
| 5,470,850 | 11/1995 | Foged et al. | 514/213 |
| 5,512,562 | 4/1996 | Hohlweg et al. | 514/215 |

FOREIGN PATENT DOCUMENTS 0 347 672    12/1989    (EP) .

OTHER PUBLICATIONS

"The D1 dopamine receptor antogonist SCH 23390 enhances REM sleep in the rat," p. 53, The Abstract No. 536b, Neuropharmacology 1990.

"Differential Effects of Dopamine D–1 and D–2 Receptor Antagonist Antipsy—chotics on Sleep–Wake Patterns in the Rat," pp 726–731, Journal of Pharmacology and Experimental Therapeutics. vol. 266, No. 2, 1993.

*Primary Examiner*—Zohreh Fay
(74) *Attorney, Agent, or Firm*—Finnegan, Henderson, Farabow, Garrett & Dunner, L.L.P.

(57) ABSTRACT

The present invention provides novel uses of the compounds of general formula (I) wherein $R^3$ is hydrogen, alkyl or cycloalkyl; $R^4$ is hydrogen or $R^4$ together with $R^{10}$ represents a bridge; $R^7$ is hydroxy or alkoxy; $R^{10}$, $R^{11}$, $R^{12}$ independently repent hydrogen, trifluoromethyl, halogen or alkyl; or $R^{10}$ together with $R^{11}$ represents a bridge, or $R^{11}$ together with $R^{12}$ represents a bridge the bridge in both cases being chosen among —O—$CH_2$—$CH_2$—, —O—$CH_2$—$CH_2$—$CH_2$—, —O—CH=CH—, —$CH_2$—$CH_2$—$CH_2$—, —$CH_2$—CH=CH— or —$CH_2$—$CH_2$—$CH_2$—$CH_2$—; $R^{13}$ is hydrogen, halogen or alkyl; and pharmaceutically acceptable salts thereof in combination with a pharmaceutically acceptable carrier for the manufacture of a pharmaceutical composition for treatment of sleep disorders and/or sleep disturbances.

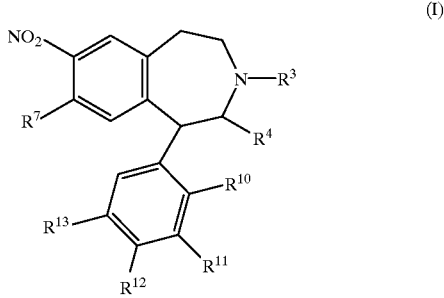

(I)

19 Claims, No Drawings

USE OF 2,3,4,5-TETRAHYDRO-1H-3-BENZAZEPINES FOR THE MANUFACTURE OF A PHARMACEUTICAL COMPOSITION FOR THE TREATMENT OF SLEEP DISORDERS

This application claim benefit to provisional application 60/041,509 Mar. 24, 1997.

FIELD OF THE INVENTION

The present invention relates to the use of compounds of the general formula I for the treatment of patients suffering from sleep disorders and/or sleep disturbances. The present invention also embraces pharmaceutical compositions comprising these compounds and methods of using the compounds and their pharmaceutical compositions.

BACKGROUND OF THE INVENTION

Sleep disorders and sleep disturbances are those known to be included in the definition by those skilled in the art, which includes e.g. insomnia, agitation, restlessness.

Benzodiazepines are widely used in the pharmacological treatment of sleep disorders and/or sleep disturbances. These compounds are endowed with numerous side effects such as amnesia, induction of tolerance and high abuse potential. Thus there exists a need for a compound in the treatment sleep disorders and/or sleep disturbances which causes less side effects than known compounds.

Preclinical experiments have shown that dopamine D1 receptor antagonists, including NNC 0756 ((+-8-chloro-7-hydroxy-3-methyl-5-(2,3-dihydrobenzofuran-7-yl)-2,3,4,5-tetrahydro-1H-3-benzazepine) markedly enhance the time spent in sleep through an increase in both REM and non-REM sleep ("Differential effects of dopamine D1 and D2 receptor antagonist antipsychotics on sleep-wake patterns in the rat", Ongini et al. (1993), Journ. Pharm. Exp. Ther., 266 (2), 726–731) whereas the dopamine D1 receptor agonist SKF 38393 reduced the amount of REM sleep and increased the duration of wakefulness ("The dopamine D1 receptor is involved in the regulation of REM sleep in the rat", Trampus et al. (1991), Eur. Journ. Pharm., 194, 189–194).

Ideally, a hypnotic should have a short half life, so that the compound, when administered at bed time, is cleared from the body in the morning. Therefore, compounds like NNC 0756, having a relatively long half life, is not well suited with respect to this indication.

In EP 5,298 and EP 5,299, 7-hydroxy-2,3,4,5-tetrahydro-1H-3-benzazepine derivatives are described. It is stated that these compounds have antipsychotic and antidepressive effects.

In European Patent No. 0200455, 8-chloro-2,3,4,5-tetrahydro-1H-3-benzazepines including NNC 0756 (+)-8-chloro-7-hydroxy-3-methyl-5-(2,3-dihydrobenzofuran-7-yl)-2,3,4,5-tetrahydro-1H-3-benzazepine are described These compounds are described as dopamine antagonists having antipsychotic and antidepressive effects.

European Patent No. 0347672 describes 8-nitro-2,3,4,5-tetrahydro-1H-3-benzazepines. These compounds are described as dopamine antagonists useful as neuroleptics in the treatment of various mental disorders, e.g manic-depressive disorders. There is no disclosure in the application of using the compounds to treat sleep disorders.

One object of the present invention is to provide compounds which can effectively be used in the treatment or prevention of sleep disorders and/or sleep disturbances, e.g. insomnia, and which have a short half life, so that the compounds, when administered at bed time, are cleared from the body in the morning.

DESCRIPTION OF THE INVENTION

It has, surprisingly, been found that compounds of the general formula I

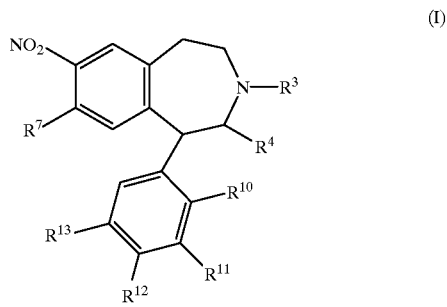

(I)

wherein
$R^3$ is hydrogen, $C_{1-4}$-alkyl or $C_{3-7}$-cycloalkyl; $R^4$ is hydrogen or $R^4$ together with $R^{10}$ represents a bridge which connects the positions to which $R^4$ and $R^{10}$ are linked, said bridge being —$CH_2$—$CH_2$—, —CH=CH—, —O—$CH_2$— or —S—$CH_2$—, provided that when the bridge contains a heteroatom, the bridge member linked to the benzazepine nucleus is always a carbon atom;
$R^7$ is hydroxy or $C_{1-4}$-alkoxy;
$R^{10}$, $R^{11}$, $R^{12}$ independently represent hydrogen, trifluoromethyl, halogen or a straight or branched $C_{1-4}$-alkyl; or $R^{10}$ together with $R^4$ represents a bridge as described in connection with the definition of $R^4$; or $R^{10}$ together with $R^{11}$ represents a bridge, or $R^{11}$ together with $R^{12}$ represents a bridge, the bridge in both cases being chosen among —O—$CH_2$—$CH_2$—, —O—$CH_2$—$CH_2$—$CH_2$—, —O—CH=CH—, —$CH_2$—$CH_2$—$CH_2$—, —$CH_2$—CH=CH— or —$CH_2$—$CH_2$—$CH_2$—$CH_2$—;
$R^{13}$ is hydrogen, halogen or $C_{1-4}$-alkyl;
or a pharmaceutically acceptable salt thereof, can be used for the manufacture of a pharmaceutical composition for the treatment or prevention of sleep disorders and/or sleep disturbances.

Thus the compounds of the above general formula I can be used in methods for treating or preventing sleep disorders and/or sleep disturbances.

It has been demonstrated that that the compounds of formula I are useful in the treatment or prevention of sleep disorders and/or sleep disturbances, such as insomnia, i.e. delay of sleep onset, difficulty staying asleep, awakening too early.

Within the present invention, compounds of formula I are used for treatment or prevention of sleep disorders and/or sleep disturbances in a patient.

Within its scope the invention includes all optical isomers of compounds of formula I, some of which are optically active, and also their mixtures including racemic mixture thereof.

The scope of the invention also includes all tautomeric forms of the compounds of formula I.

As used herein, the terms "$C_{1-4}$-alkyl" includes straight or branched chain alkyl radicals containing from 1 to 4 carbon atoms, such as methyl, ethyl, n-propyl, isopropyl, n-butyl, tert-butyl and the like.

The term "$C_{3-7}$-cycloalkyl" as used herein refers to a radical of a saturated cyclic hydrocarbon with the indicated number of carbons such as cyclopropyl, cyclobutyl, cyclopentyl or cyclohexyl.

The term "$C_{1-4}$-alkoxy" includes straight or branched chain alkoxy radicals containing from 1 to 4 carbon atoms, such as methoxy, ethoxy, n-propoxy, isopropoxy, n-butoxy, tert-butoxy and the like.

"Halogen" includes chloro, fluoro, bromo and iodo.

Preferred compounds include those in which $R^3$ is $C_{1-4}$-alkyl, especially methyl; $R^4$ is hydrogen or $R^4$ together with $R^{10}$ represents a bridge being —$CH_2$—$CH_2$— or —CH=CH—; $R^7$ is hydroxy; $R^{10}$ $R^{11}$, $R^{12}$ independently represent hydrogen, halogen, trifluormethyl or methyl; or $R^{10}$ together with $R^{11}$ represents a bridge being —O—$CH_2$—$CH_2$—, —O—CH=CH—, —$CH_2$—$CH_2$—$CH_2$— or —$CH_2$—CH=CH—, or $R^{11}$ together with $R^{12}$ represents a bridge being —O—$CH_2$—$CH_2$—, —O—CH=CH—, —$CH_2$—$CH_2$—$CH_2$— or —$CH_2$—CH=CH—; $R^{13}$ is hydrogen.

To be included by this invention are all pharmaceutically acceptable salts of the mentioned compounds of formula I.

As used herein the term "patient" includes any mammal which could benefit from treatment of sleep disorders. The term particularly refers to a human patient, but is not intended to be so limited.

The compounds of formula I are prepared according to known methods, such as those described in European Patent No. 0347672, the contents of which are incorporated herein by reference.

Within the present invention, the compounds of formula I may be prepared in the form of pharmaceutically acceptable salts, especially acid addition salts, including salts of organic acids and mineral acids. Examples of such salts include salts of organic acids such as formic acid, fumaric acid, acetic acid, propionic acid, lactic acid, oxalic acid, succinic acid, malonic acid, phthalic acid, fumaric acid, mandelic acid, methane-sulfonic acid, ethane-sulfonic acid, .malic acid, tartaric acid, citric acid, benzoic acid, salicylic acid and the like. Suitable inorganic acid-addition salts include salts of hydrochloric acid, hydrobromic acid, sulphuric acid and phosphoric acid and the like. The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of formula I and their salts are useful within human and veterinary medicine, for example, in the treatment of patients suffering from a sleep disorder and/or sleep disturbance. For use within the present invention, the compounds of formula I and their pharmaceutically acceptable salts are formulated with a pharmaceutically acceptable carrier to provide a medicament for parenteral, oral, nasal, rectal, subdermal or intradermal or transdermal administration according to conventional methods. Formulations may further include one or more diluents, fillers, emulsifiers, preservatives, buffers, excipients, etc. and may be provided in such forms as liquids, powders, emulsions, suppositories, liposomes, transdermal patches, controlled release, dermal implants, tablets, etc. One skilled in this art may formulate the compounds of formula I in an appropriate manner, and in accordance with accepted practices, such as those disclosed in *Remington's Pharmaceutical Sciences*, Gennaro, ed., Mack Publishing Co., Easton, Pa., 1990.

Oral administration is preferred. Thus, the active compound of formula I is prepared in a form suitable for oral administration, such as a tablet or capsule. Typically, a pharmaceutically acceptable salt of the compound of formula I is combined with a carrier and moulded into a tablet Suitable carriers in this regard include starch, sugars, dicalcium phosphate, calcium stearate, magnesium stearate and the like. Such compositions may further include one or more auxiliary substances, such as wetting agents, emulsifiers, preservatives, stabilizers, colouring additives, etc.

Pharmaceutical compositions containing a compound of formula I may be administered ones or more times per day or week An effective amount of such a pharmaceutical composition is the amount that provides a clinically significant effect against one or more sleep disorders and/or disturbances. Such amounts will depend, in part, on the particular condition to be treated, age, weight, and general health of the patient, and other factors evident to those skilled in the art A typical daily dosage is suitably from about 0.01 mg to about 100 g, preferably from about 1 to about 1000 mg, especially from about 10 to about 100 mg per patient per day.

The pharmaceutical compositions containing a compound of formula I may be administered in unit dosage form one or more times per day or week.

PHARMACOKINETIC EXPERIMENTS

NNC 0756 (80 mg) and another dopamine D1 receptor antagonist, the compound of Example 4 (25 mg), were administered to two and three men, respectively. Serum concentrations of the compounds were measured 1.5 and 6.0 hours following oral administration of the compound of Example 4 and 1.5 and 8.0–8.8 hours following oral administration of NNC 0756.

Results

Surprisingly, in contrast to the fact that serum concentration of NNC 0756 at 8.0–8.8 hours after drug administration was decreased to about 35% of the serum concentration measured 1.5 hours after administration of NNC 0756, it has been found that the serum concentration of the compound of Example 4, 6 hours after drug administration, was decreased to about 10% of the serum concentration measured 1.5 hours after drug administration.

Therefore, based on the improved kinetic profile of the compound of Example 4, i.e. shorter elimination time, compared to the kinetic profile of NNC 0756, the compounds of the present invention have a shorter half life, making the compounds of the present invention useful in the treatment of sleep disorders and/or sleep disturbances.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLES

Example 1

5-(2-fluorophenyl)-7-hydroxy-3-methyl-8-nitro-2,3,4,5-tetrahydro-1H-3-benzazepine A) 5-(2-fluorophenyl)-7-hydroxy-3-methyl-2,3,4,5-tetrahydro-1H-3-benzazepine:

10.0 mg 8-chloro-5-(2-fluorophenyl)-7-hydroxy-3-methyl-2,3,4,5-tetrahydro-1H-3-benzazepine was dissolved in 500 ml acetic acid containing sodium acetate. Palladium-on-carbon was added and the suspension was heated to 60° C. Under vigorous stirring hydrogen was led through the suspension giving after 48 h 7.9 g crystalline compound. Yield 72%.

NMR: >CH—OH 4.45 dd; $C_6H$ 5.95 d; $C_8H$ 6.45 d; $C_7OH$ 8.75 s ppm. respectively.

This compound was used for the next step without further purification.

B) 5-(2-fluorophenyl)-7-hydroxy-3-methyl-8-nitro-2,3,4,5-tetrahydro-1H-3-benzazepine:

5.0 g 5-(2-fluorophenyl)-7-hydroxy-3-methyl-2,3,4,5-tetrahydro-1H-3-benzazepine was dissolved in 90 ml of a mixture of acetic acid and cooled in ice-water bath 0° C. Under stirring was added 1.7 ml fuming nitric acid and the mixture was stirred in the cold for 1 h. The reaction mixture was neutralized (pH 7.9) and the precipitate was extracted with ethyl acetate, dried and evaporated. After column chromatography (kieselgel/$CH_2Cl_2$: $CH_3OH$ 95:5) was isolated yellow crystals. M.p. 90–94° C. (dec). NMR: $C_5H$ 4.61 d; $C_6H$ g 41% 6 s and $C_9H$ 7.88 s ppm. respectively.

Example 2

7-hydroxy-3-methyl-8-nitro-5-(3-trifluromethylphenyl)-2,3,4,5-tetrahydro-1H-3-benzazepine A) 7-hydroxy-3-methyl-5-(trifluoromethylphenyl)-2,3,4,5-tetrahydro-1H-3-benzazepine was prepared in analogy with the method A in example 1. Yield 2.5 g, 81%. NMR: $C_5H$ 4.25 dd; $C_6H$ 5 dd; $C_5H$ 6.5 dd; $C_9H$ 7.0 ppm. respectively.

This compound was used for the next step without further purification.

B) 7-hydroxy-3-methyl-8-nitro-(3-trifluoromethylphenyl)-2,3,4,5-tetrahydro-1H-3-benzazepine is prepared in analogy with method B in example 1 giving 0.4 g (14%). M.p. 205–210° C. (dec). NMR: $C_5H$ 5.08 d; $C_6H$ 6.5 s; $C_9H$ 7.88 ppm. respectively.

Example 3

7-hydroxy-3-methyl-8-nitro-5-(2-methylphenyl)-2,3,4,5-tetrahydro-1H-3-benzazepine A) 1 g of 7-hydroxy-3-methyl-5-(2-methylphenyl)-2,3,4,5-tetrahydro-1H-3benzazepine was dissolved in a mixture of acetic acid (5 ml) and acetic anhydride (5 ml). To this mixture was added fuming nitric acid and the reaction mixture was stirred at room temperature for 2 h. Crushed ice was added to the reaction mixture and sodium hydroxide solution (6 N) was added slowly to pH 7.5. This mixture was extracted with ethyl acetate, the combined organic layer was dried and evaporated giving a solid which was purified by column chromatography (kieselgel: $CH_2Cl_2/CH_3OH$ 98/2). Yield: 300 mg (27%). NMR: $C_5H$ 4.58 d; $C_6H$ 6.11 s; $C_9H$ 7.64 s ppm. respectively.

This compound was used directly for the next step.

B) 300 mg of 7-methoxy-3-methyl-8-nitro-5-(2'-methylphenyl)-2,3,4,5-tetrahydro-1H-3-benzazepine was dissolved in MEOH and cooled to −70° C. 1 g $BBr_3$ was added slowly and the mixture was stirred for 1 h at −70° C., and stirring was continued for 1 h. Methanol was slowly added to destroy the excess of $BBr_3$ and the mixture was evaporated to dryness. The raw material was purified by column chromatography (kieselgel, $CH_2Cl_2/CH_3OH$: 98/2) giving 110 mg of the desired compound. M.p. 59–61 NMR: $C_5H$ 5.10 d; $C_6H$ 6.20 s; $C_9H$ 8.05 s ppm. respectively.

Example 4

(+)-5-(2,3-dihydrobenzofuran-7-yl)-7-hydroxy-3-methyl-8-nitro-2,3,4,5-tetrahydro-1H-3-benzazepine A) (+)-5-(2,3-dihydrobenzofuran-7-yl)-7-hydroxy-3-methyl-2,3,4,5-tetrahydro-1H-3-benzazepine 6.55 g, (0.020 mol) (+)-5-(benzofuran-7-yl)8-chloro-7-hydroxy-3-methyl-2,3,4,5-tetrahydro-1H-3-benzazepine was dissolved in 1.0 N sodium hydroxide (100 ml, 0.100 mol) and water (100 ml). 10% palladium-on-carbon (3.0 g) was added, and the resulting suspension was stirred under hydrogen at 20° C. and 100 kPa for 5 days. The reaction mixture was filtered and the filtercake was thoroughly washed with 0.3 N hydrochloric acid (70 ml) and methanol (135 ml). The pH of the combined filtrate and washings was brought to 8.0 and the resulting suspension was filtered. The filtercake was washed with water/methanol (1/1) and dried in vacuo at 40° C. to give 3.45 g (76% of the theoretical yield) of the desired compound as white crystals.) M.p. 227–30° C.

B) 3.0 g (3.03 mmol) (+5-(2,3-dihydrobenzofuran-7-yl)-7-hydroxy-3-methyl-2,3,4,5-tetrahydro-1H-3benzazepine was dissolved in a mixture of methylene chloride (25 ml) and acetic acid (75) at 10° C. and fuming nitric acid (0.5 ml) was added. The reaction mixture was stirred for 2 h at 10–15° C. Then the reaction mixture was evaporated to about 20 ml and diluted with water (100 ml). pH was adjusted to 8.5 and the water phase was extracted twice with methylene chloride. The combined organic phases were dried and evaporated to give 2.1 g of crude product.

Purification by column chromatography (methylene chloride/methanol 9/1) gave 1.9 g of (+)-5-(2,3-dihydrobenzofuran-7-yl)-7-hydroxy-3-methyl-8nitro-2,3,4,5-tetrahydro-1H-3-benzazepine as white crystals. M.p. 122–3° C.

| Calc.: | 67.0% C | 5.9% H | 8.2% N |
|---|---|---|---|
| Found: | 66.8% C | 6.1% H | 8.1% N |

Example 5

7-hydroxy-5-(5-indanyl)-3-methyl-8-nitro-2,3,4,5-tetrahydro-1H-3-benzazepine

A) 7-hydroxy-5-(5-indanyl)-3-methyl-2,3,4,5-tetrahydro-1H-3-benzazepine was prepared in analogy with example 1A. Yield: 1.05 g (92%). M.p. 213–22° C. (dec). NMR: $C_5H$ 4.6 d; $C_6H$ 5.65 d; $C_9H$ 6.4 dd; $C_9H$ 6.9 d ppm respectively.

B) 7-hydroxy-5-(5-indanyl)-3-methyl-nitro-2,3,4,5-tetrahydro-1H-3-benzazepine was prepared in analogy with example 1B. Yield: 0.45 g (39%). M.p. 58–63° C. NMR: $C_5H$ 4.66 d; $C_6H$ 6.06 s; $C_9H$ 7.8 s ppm. respectively.

| Calc.: | 70.99% C | 6.55% H | 7.67% N |
|---|---|---|---|
| Found: | 70.43% C | 6.94% H | 7.77% N |

Example 6 trans-[6,7,7a,8,9,13b]-hexahydro-2-hydroxy-7-methyl-3-nitro-5H-benzo[d]naphto[2,1-b]azepine trans-[6,7,7a,8,9,13b]-hexahydro-2-hydroxy-7-methyl-5H-benzo[d]naphto[2,1-b]azepine (642 mg) was dissolved in a mixture of 40 ml acetic acid and 4 ml of water, cooled to about 5° C. and treated with 0.5 ml of concentrated nitric acid. After 1 h the reaction mixture was neutralized to pH 7.8. The precipitate was collected and purified by column chromatography (silicagel; THF+1% TEA) giving 95 mg (15% th). M.p. 115–20° C. NMR: $C_1H$ 6.06 s; $C_4H$ 7.8 s; $C_{13b}H$ 4.75 d ppm. respectively.

What is claimed is:

1. A method for treating sleep disorders and/or sleep disturbances which method comprises administering to a person in need thereof a clinically effective amount of a benzazepine compound of the formula (1)

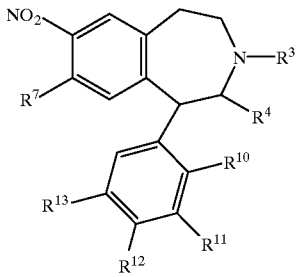

(I)

wherein
- $R^3$ is hydrogen, $C_{1-4}$-alkyl or $C_{3-7}$-cycloalkyl; $R^4$ is hydrogen or $R^4$ together with $R^{10}$ represents a bridge which connects the positions to which $R^4$ and $R^{10}$ are linked, said bridge being —$CH_2$—$CH_2$—, —CH=CH—, —O—$CH_2$— or —S—$CH_2$—, provided that when the bridge contains a heteroatom, the bridge member linked to the benzazepine nucleus is always a carbon atom;
- $R^7$ is hydroxy or $C_{1-4}$-alkoxy;
- $R^{10}$, $R^{11}$, $R^{12}$ independently represent hydrogen, trifluoromethyl, halogen or a straight or branched $C_{1-4}$-alkyl; or $R^{10}$ together with $R^4$ represents a bridge as described above; or $R^{10}$ together with $R^{11}$ represents a bridge, or $R^{11}$ together with $R^{12}$ represents a bridge, the bridge in both cases being chosen among —O—$CH_2$—$CH_2$—, —O—$CH_2$—$CH_2$—$CH_2$—, —O—CH=CH—, —$CH_2$—$CH_2$—$CH_2$—, —$CH_2$—CH=CH— or —$CH_2$—$CH_2$—$CH_2$—$CH_2$—; and
- $R^{13}$ is hydrogen, halogen or $C_{1-4}$-alkyl;

or a pharmaceutically acceptable salt thereof.

2. The method of claim 1 wherein the sleep disorder is insomnia.

3. The method of claim 1 or 2 wherein $R^3$ is $C_{1-4}$-alkyl, $R^4$ is hydrogen or $R^4$ together with $R^{10}$ represents a bridge being —$CH_2$—$CH_2$— or —CH=CH—; $R^7$ is hydroxy; $R^{10}$, $R^{11}$, $R^{12}$ independently represent hydrogen, halogen, trifluoromethyl or methyl; or $R^{10}$ together with $R^{11}$ represents a bridge being —O—$CH_2$—$CH_2$—, —O—CH=CH—, —$CH_2$—$CH_2$—$CH_2$— or —$CH_2$—CH=CH—, or $R^{11}$ together with $R^{12}$ represents a bridge being —O—$CH_2$—$CH_2$—, —O—CH=CH—, —$CH_2$—$CH_2$—$CH_2$— or —$CH_2$—CH=CH—; and $R^{13}$ is hydrogen.

4. The method of claim 1 wherein $R^3$ is $C_{1-4}$-alkyl.

5. The method of claim 1 wherein $R^3$ is methyl.

6. The method of claim 1 wherein $R^4$ is hydrogen.

7. The method of claim 1 wherein $R^4$ together with $R^{10}$ represents a bridge being —$CH_2$—$CH_2$— or —CH=CH—.

8. The method of claim 1 wherein $R^7$ is hydroxy.

9. The method of claim 1 wherein $R^{10}$, $R^{11}$, $R^{12}$ independently represent hydrogen, halogen, methyl or trifluoromethyl.

10. The method of claim 1 wherein $R^{10}$ together with $R^{11}$ represents a bridge being —O—$CH_2$—$CH_2$— or —O—CH=CH—.

11. The method of claim 1 wherein $R^{10}$ together with $R^{11}$ represents a bridge being —$CH_2$—$CH_2$—$CH_2$— or —$CH_2$—CH=CH—.

12. The method of claim 1 wherein $R^{11}$ together with $R^{12}$ represents a bridge being —O—$CH_2$—$CH_2$— or —O—CH=CH—.

13. The method of claim 1 wherein $R^{11}$ together with $R^{12}$ represents a bridge being —$CH_2$—$CH_2$—$CH_2$— or —$CH_2$—CH=CH—.

14. The method of claim 1 wherein $R^{13}$ is hydrogen.

15. The method of claim 1 wherein the compound is (+)-5-(2,3-dihydrobenzofuran-7-yl)-7-hydroxy-3-methyl-8-nitro-2,3,4,5-tetrahydro-1H-3-benzazepine.

16. The method of claim 1 wherein the compound is in a form suitable for oral administration.

17. The method of claim 1 wherein the compound is administered in a dose in the range from about 0.01 mg to about 100 g per person per day.

18. The method of claim 17 wherein the compound is administered in a dose of from about 1 to 1000 mg per person per day.

19. The method of claim 18 wherein the compound is administered in a dose of from about 10 to 100 mg per person per day.

* * * * *